United States Patent
Delmotte

(10) Patent No.: US 8,641,661 B2
(45) Date of Patent: Feb. 4, 2014

(54) MIXING SYSTEM, KIT AND MIXER ADAPTER

(75) Inventor: Yves A. Delmotte, Neufmaison (BE)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 120 days.

(21) Appl. No.: 12/984,596

(22) Filed: Jan. 4, 2011

(65) Prior Publication Data

US 2011/0166596 A1   Jul. 7, 2011

Related U.S. Application Data

(60) Provisional application No. 61/292,369, filed on Jan. 5, 2010.

(51) Int. Cl.
*A61M 37/00* (2006.01)

(52) U.S. Cl.
USPC .................................... 604/82; 604/416

(58) Field of Classification Search
USPC .................................... 604/82, 416
See application file for complete search history.

(56) References Cited

U.S. PATENT DOCUMENTS

| | | | |
|---|---|---|---|
| 49,345 A | 8/1865 | Hervey | |
| 1,496,345 A | 6/1924 | Lichtenthaeler | |
| 2,584,827 A | 2/1952 | Bailey | |
| 2,747,844 A | 5/1956 | Slayter | |
| 3,477,432 A | 11/1969 | Shaw | |
| 3,548,825 A | 12/1970 | Shaw | |
| 3,861,652 A | 1/1975 | Clark et al. | |
| 4,068,830 A | 1/1978 | Gray | |
| 4,316,673 A * | 2/1982 | Speer | 366/337 |
| 4,329,067 A * | 5/1982 | Goudy, Jr. | 366/152.1 |
| 4,475,821 A | 10/1984 | Koch et al. | |
| 4,538,920 A | 9/1985 | Drake | |
| 4,568,725 A | 2/1986 | Boisson et al. | |
| 4,631,055 A | 12/1986 | Redl et al. | |
| 4,743,229 A * | 5/1988 | Chu | 604/82 |
| 4,776,704 A * | 10/1988 | Kopunek et al. | 366/184 |

(Continued)

FOREIGN PATENT DOCUMENTS

DE   20307153   9/2003
EP   0839498    5/1998

(Continued)

OTHER PUBLICATIONS

DivibaX® Device, Promens hf, Kopavogur, Iceland (circa 2008, 3 pp.).

(Continued)

*Primary Examiner* — Nicholas Lucchesi
*Assistant Examiner* — Niyati D Shah
(74) *Attorney, Agent, or Firm* — Marshall, Gerstein & Borun LLP

(57) ABSTRACT

A system includes a cylinder having a bore with a piston disposed therein, the piston moveable along the bore of the cylinder and having a passage therethrough. The system also includes a mixer disposed in the passage in the piston and including at least one porous mixing device, the at least one porous mixing device comprising a three-dimensional lattice defining a plurality of tortuous, interconnecting passages therethrough, and having physical characteristics to sufficiently mix the first and second components, which characteristics include a selected one or more of mean flow pore size, thickness and porosity.

15 Claims, 6 Drawing Sheets

(56) References Cited

U.S. PATENT DOCUMENTS

| | | |
|---|---|---|
| 4,846,405 A | 7/1989 | Zimmermann |
| 4,978,336 A | 12/1990 | Capozzi et al. |
| 5,116,315 A | 5/1992 | Capozzi et al. |
| 5,181,909 A | 1/1993 | McFarlane |
| 5,193,907 A | 3/1993 | Faccioli et al. |
| 5,364,595 A | 11/1994 | Smith |
| 5,368,563 A | 11/1994 | Lonneman et al. |
| 5,443,183 A | 8/1995 | Jacobsen et al. |
| 5,474,540 A | 12/1995 | Miller et al. |
| 5,531,683 A | 7/1996 | Kriesel et al. |
| 5,556,580 A | 9/1996 | Suddith |
| 5,582,596 A | 12/1996 | Fukunaga et al. |
| 5,605,255 A | 2/1997 | Reidel et al. |
| 5,614,153 A | 3/1997 | Homberg |
| 5,665,067 A | 9/1997 | Linder et al. |
| 5,785,682 A * | 7/1998 | Grabenkort ............ 604/82 |
| 5,788,670 A | 8/1998 | Reinhard et al. |
| 5,989,215 A | 11/1999 | Delmotte et al. |
| 6,045,757 A | 4/2000 | Moriarty et al. |
| 6,054,122 A | 4/2000 | MacPhee et al. |
| 6,062,722 A | 5/2000 | Lake |
| 6,074,663 A | 6/2000 | Delmotte et al. |
| 6,132,396 A | 10/2000 | Antanavich et al. |
| 6,186,982 B1 | 2/2001 | Gross et al. |
| 6,328,229 B1 | 12/2001 | Duronio et al. |
| 6,383,422 B1 | 5/2002 | Hoffschmidt |
| 6,454,739 B1 | 9/2002 | Chang |
| 6,461,325 B1 | 10/2002 | Delmotte et al. |
| 6,461,361 B1 | 10/2002 | Epstein |
| 6,548,729 B1 | 4/2003 | Seelich et al. |
| 6,561,200 B1 | 5/2003 | Fournel et al. |
| 6,562,002 B1 | 5/2003 | Taylor |
| 6,566,145 B2 | 5/2003 | Brewer |
| 6,585,696 B2 | 7/2003 | Petersen et al. |
| 6,599,515 B1 | 7/2003 | Delmotte |
| 6,620,125 B1 | 9/2003 | Redl |
| 6,802,822 B1 | 10/2004 | Dodge |
| 6,835,186 B1 | 12/2004 | Pennington et al. |
| 6,884,232 B1 | 4/2005 | Hagmann et al. |
| 6,887,974 B2 | 5/2005 | Pathak |
| 6,921,381 B2 | 7/2005 | Spero et al. |
| 6,965,014 B1 | 11/2005 | Delmotte et al. |
| 7,077,835 B2 | 7/2006 | Robinson et al. |
| 7,135,027 B2 | 11/2006 | Delmotte |
| 7,211,651 B2 | 5/2007 | Pathak |
| 7,328,549 B2 | 2/2008 | Kinney et al. |
| 7,560,100 B2 | 7/2009 | Pinchasi et al. |
| 7,906,118 B2 | 3/2011 | Chang et al. |
| 2005/0142162 A1 | 6/2005 | Hunter et al. |
| 2006/0009801 A1 | 1/2006 | McGurk et al. |
| 2006/0191962 A1 | 8/2006 | Redl et al. |
| 2006/0258977 A1* | 11/2006 | Lee .......................... 604/82 |
| 2008/0281271 A1 | 11/2008 | Griffiths et al. |
| 2009/0038701 A1 | 2/2009 | Delmotte |

FOREIGN PATENT DOCUMENTS

| | | |
|---|---|---|
| EP | 2002882 | 12/2008 |
| GB | 2060420 | 5/1981 |
| RU | 2191623 | 10/2002 |
| WO | WO 96/39212 | 12/1996 |
| WO | WO 00/51704 | 9/2000 |
| WO | WO 01/00261 | 1/2001 |
| WO | WO 2004/024306 | 3/2004 |
| WO | WO 2005/048977 | 6/2005 |
| WO | WO 2007/057717 | 5/2007 |
| WO | WO 2007/084919 | 7/2007 |
| WO | WO2007084919 * | 7/2007 ............ A61B 17/00 |
| WO | WO 2008/027821 | 3/2008 |

OTHER PUBLICATIONS

Gruber et al., "Alteration of Fibrin Network by Activated Protein C", *Blood*, 83:2541-8 (May 1, 1994).

Porex Porous Products Group, Interact w/Innovation . . . Discover the Advantages of Porex (circa 2007, 9 pp.).

Porex Porous Products Group, Mupor™ Membrane Applications Brief Catalog (Fairburn, GA) (circa 2000, 7 pp.).

Porex Porous Products Group, Products & Services Catalog (Fairburn, GA) (circa 2002, 24 pp.).

Porvair Filtration Group Ltd., "Developments in porous polymeric materials", (Fareham, Hampshire UK) (Sep. 2005, 1 page).

Porvair Filtration Group, Sintered Porous Materials (circa 2007, 7 pp.).

Porex Technologies, Healthcare Applications: Pipette (Fairburn, GA) (2006, 1 page).

International Search Report and Written Opinion for corresponding International Application No. PCT/US2011/020153, mailing date Aug. 23, 2011 (9pp.).

* cited by examiner

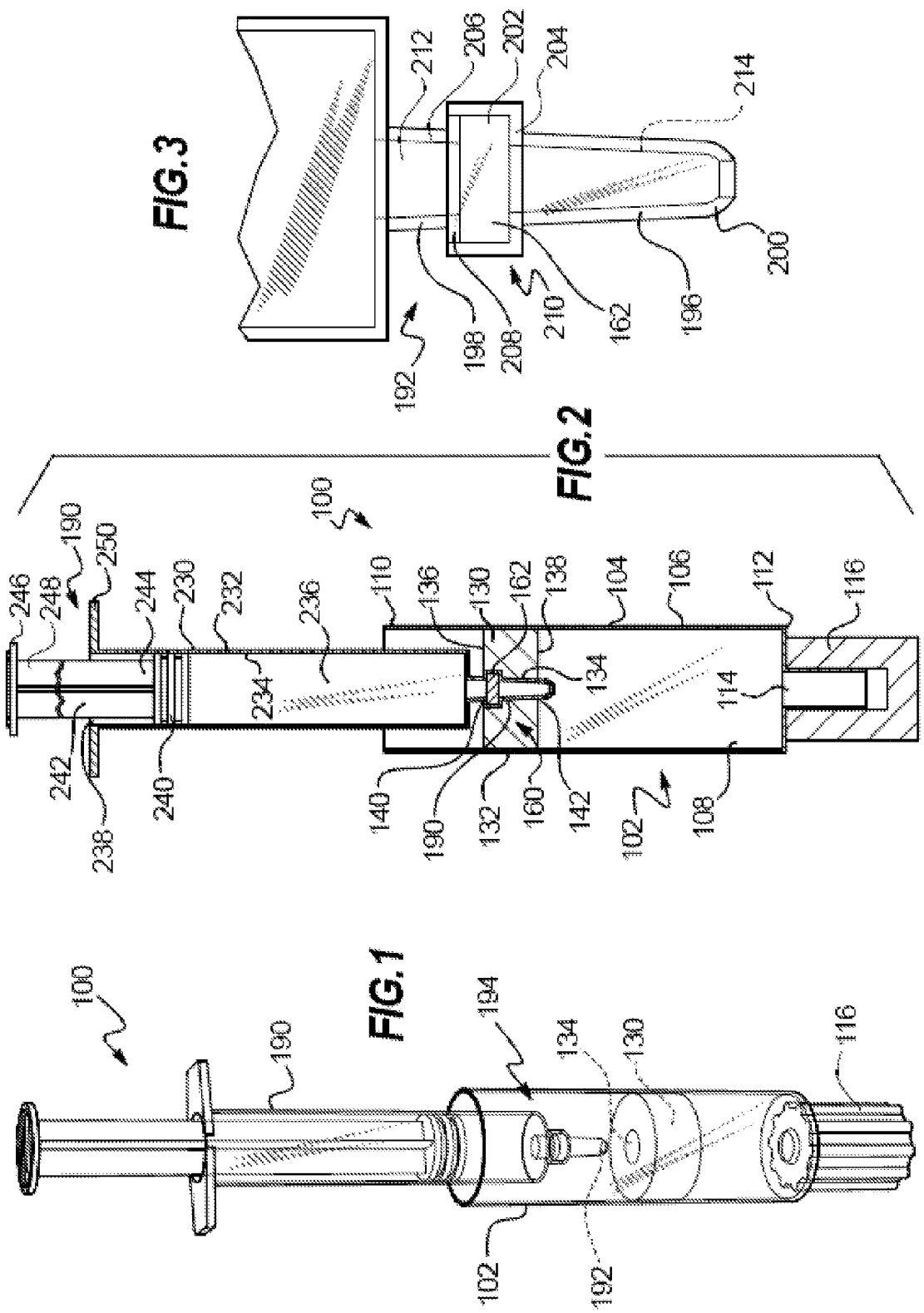

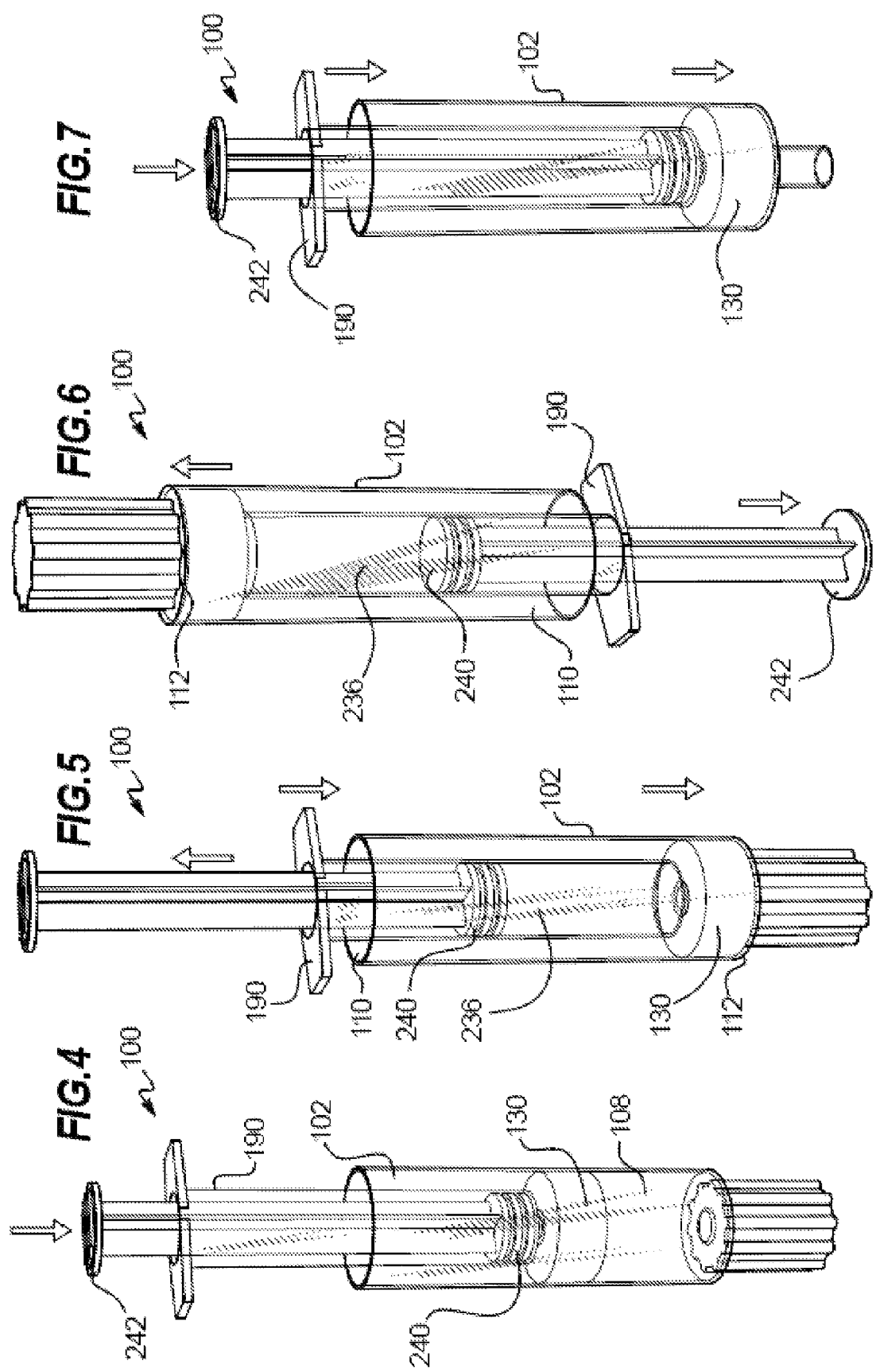

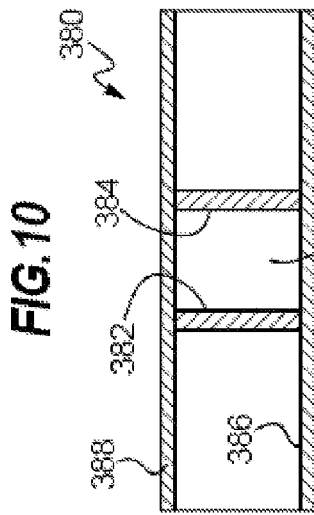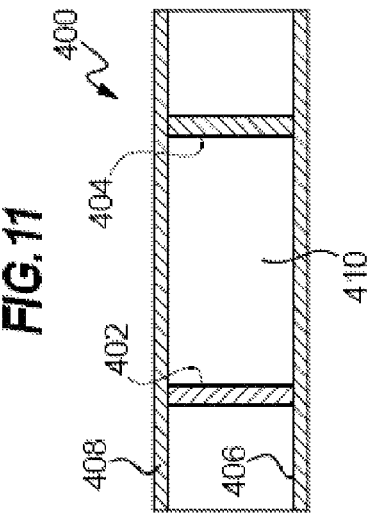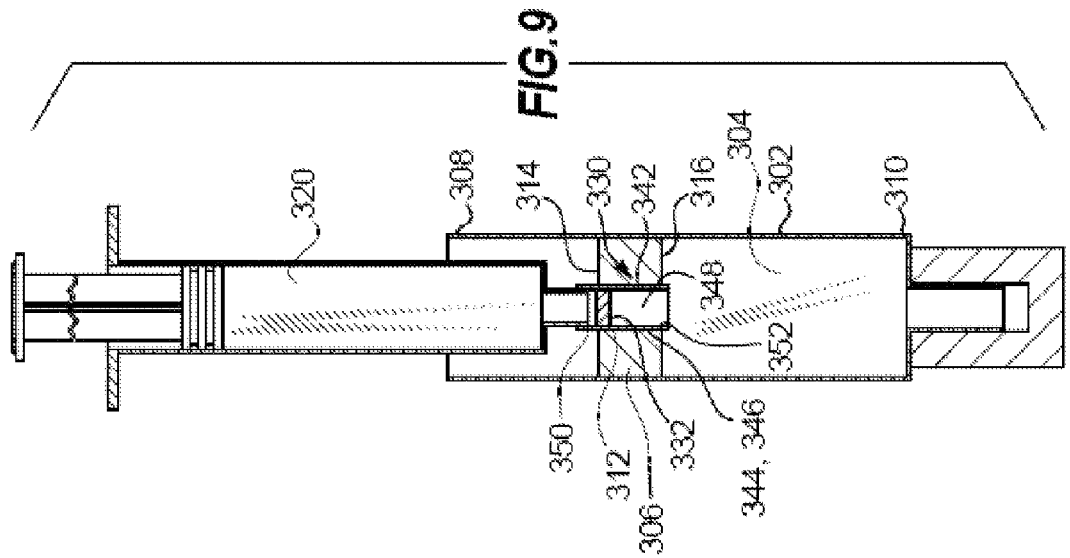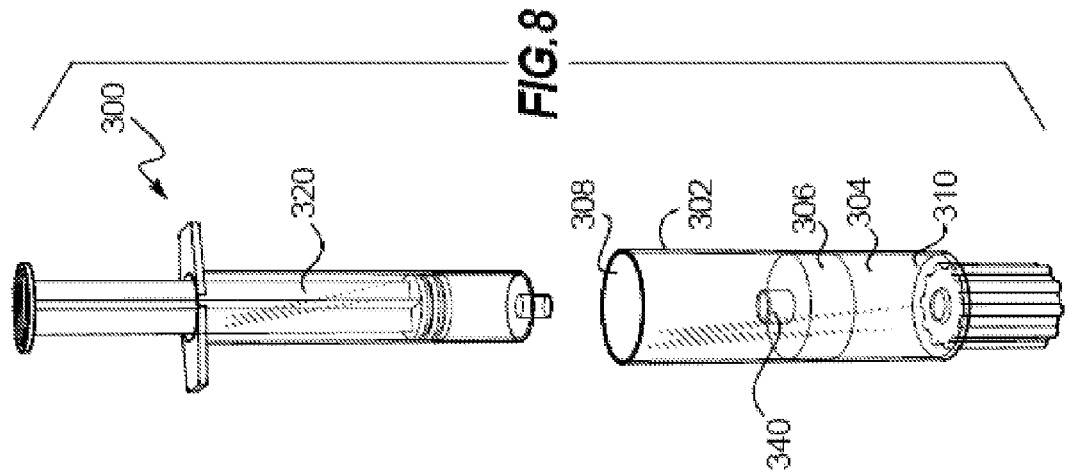

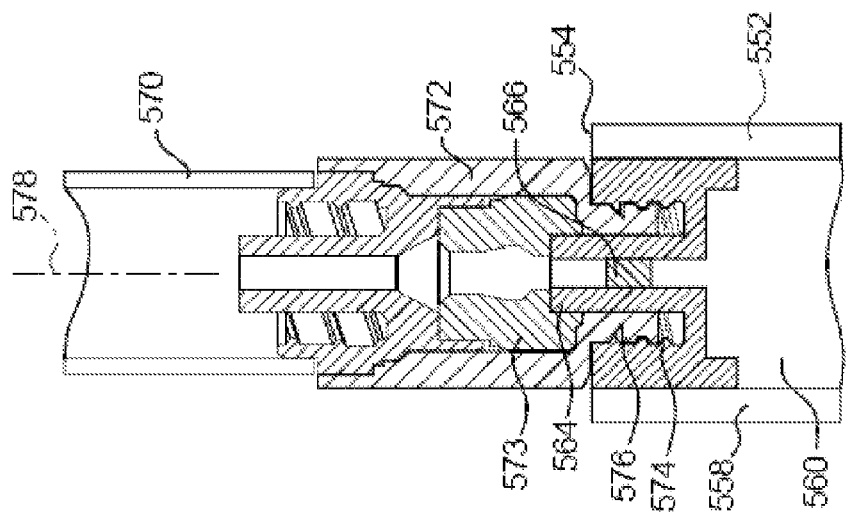
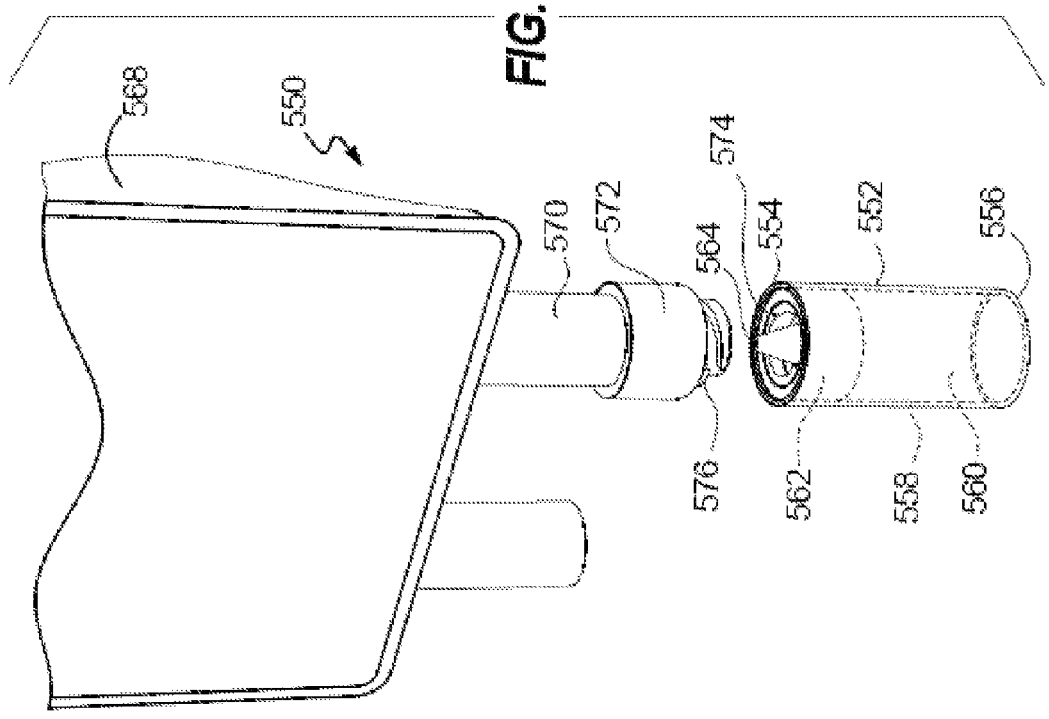

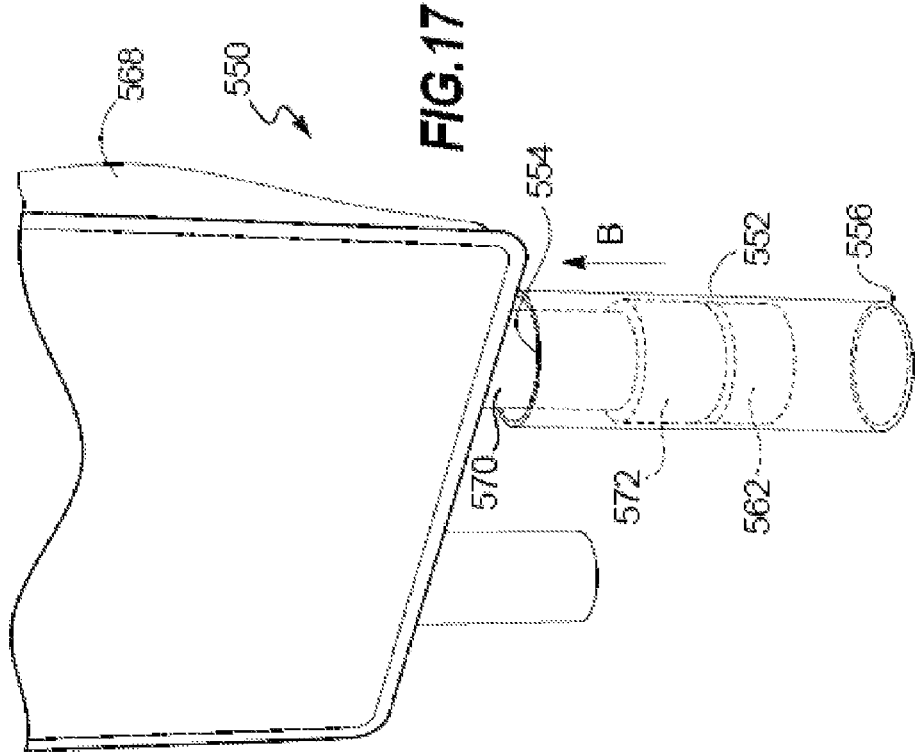
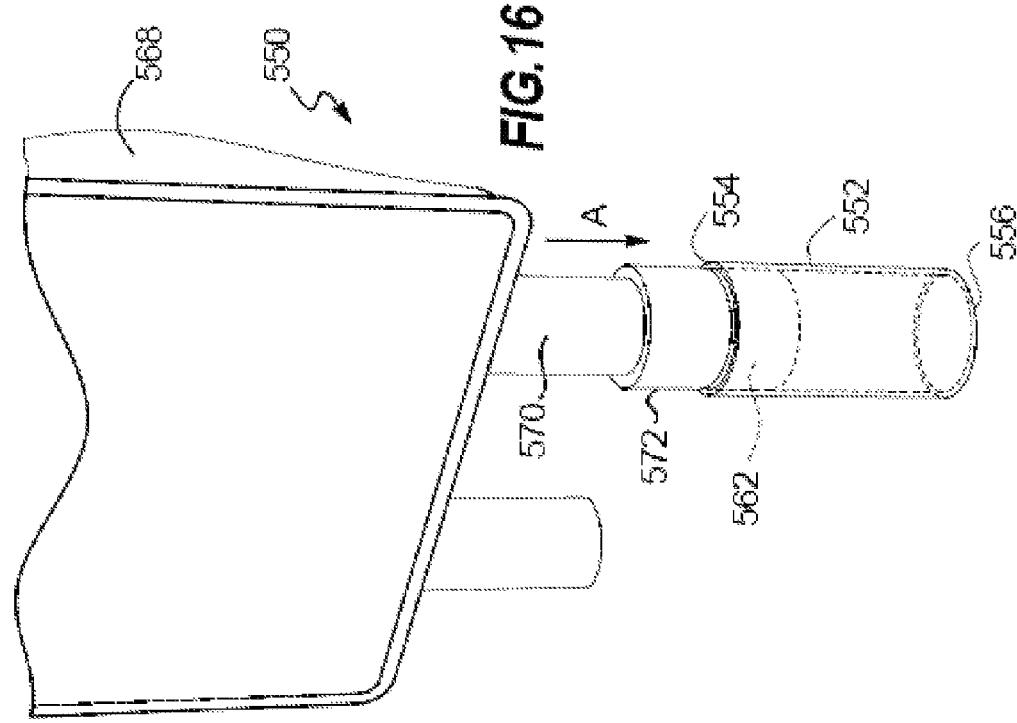

MIXING SYSTEM, KIT AND MIXER ADAPTER

This application claims the benefit of U.S. Application No. 61/292,369, filed Jan. 5, 2010, which is hereby incorporated by reference in its entirety herein.

BACKGROUND

This patent relates to a system for mixing a system of at least two components. In particular, this patent relates to a system for mixing and dispensing an at least two-component system.

In the medical field, due to long or medium term stability issues or interaction between two components, two components may need to be mixed or reconstituted shortly before administration to the patient. This mixing must be done to a degree which causes the desired solution to be formed and also will likely need to be done in a sterile environment. These two components may take several forms such as of a lyophilisate and a solvent or diluent, a liquid and a liquid, a powder and a liquid or a pair of components with one or both being frozen.

More particularly in the field of tissue sealants used to seal or repair biological tissue, a sealant is typically formed from two or more components that, when mixed, form a sealant having sufficient adhesion for a desired application, such as to seal or repair skin or other tissue. Such sealant components are preferably biocompatible, and can be absorbed by the body, or are otherwise harmless to the body, so that they do not require later removal.

For example, fibrin is a well known tissue sealant that is made from a combination of at least two primary components—fibrinogen and thrombin. Fibrinogen is used as the substrate, while thrombin is used as the catalyst, cleaving fibrinopeptides A and B to form a fibrin network. Fibrinogen and thrombin have, depending on the temperature, viscosities of about 90-300 cps and 5 cps, respectively. Upon coming into contact with each other, the fibrinogen and thrombin components interact to form the tissue sealant fibrin, which is extremely viscous.

The fibrinogen and thrombin components are typically kept in separate containers so as to be combined only just prior to application. However, because fibrinogen and thrombin have different viscosities, a complete and thorough mixing is often difficult to achieve. If the components are inadequately mixed, then the efficacy of the sealant to seal or bind tissue at the working surface may be compromised.

To overcome the difficulties of the formation of the highly viscous fibrin in the medical field, in providing tissue sealant, it has become common to provide in-line mixing of the two or more components—in lieu of batch or tank mixing of the components. Some sealant products that may provide suitable mixtures include FLOSEAL, COSEAL, TISSEEL and ARTISS sealants from Baxter Healthcare Corporation, OMINEX sealants from Johnson & Johnson and BIOGLUE sealants from Cryolife, Inc. Such sealant may be applied by a dispenser that ejects sealant directly onto the tissue or other substrate or working surface. Examples of tissue sealant dispensers are shown in U.S. Pat. Nos. 4,631,055, 4,846,405, 5,116,315, 5,582,596, 5,665,067, 5,989,215, 6,461,361 and 6,585,696, 6,620,125 and 6,802,822 and PCT Publication No. WO 96/39212, all of which are incorporated herein by reference. Further examples of such dispensers also are sold under the TISSOMAT and DUPLOJECT trademarks, which are marketed by Baxter AG. Typically, in these prior art devices, two individual streams of the components fibrinogen and thrombin are combined and the combined stream is dispensed to the work surface. Combining the streams of fibrinogen and thrombin initiates the reaction that results in the formation of the fibrin sealant.

While thorough mixing is important to fibrin formation, fouling or clogging of the dispenser tip may interfere with proper dispensing of fibrin. Such clogging or fouling may result from contact or mixing of the sealant components in a dispenser for an extended period of time prior to ejection of the sealant components from the dispensing tip. Further, the quality of mixing of the two or more components having different viscosities may vary depending on the flow rate. For example, under certain flow conditions, the components may be dispensed as a less than thoroughly mixed stream.

Frankly, inadequate mixing of the type described above is also a problem present in other medical and/or non-medical fields, where two or more components having relatively different viscosities are required to be mixed together. Such components may tend to separate from each other prior to use or be dispensed in a less than thoroughly mixed stream, due at least in part to their different viscosities, flow rates and depending on the temperature and amount of time such mixture may be stored prior to use.

Inadequate mixing may also result in un-dissolved granules which may clog downstream passageways or result in a solution that is ill suited for the application in for which the solution is intended.

Accordingly, although prior devices have functioned to various degrees in forming and dispensing mixtures, there is a continuing need to provide a mixing and dispensing system that provides reliable and thorough mixing of at least two components (such as, for example, for a tissue sealant) for application to a desired work surface or other use applications in other fields. Further, there is a desire to provide a mixing system that is not dependent on the flow rate to achieve sufficient mixing.

As set forth in more detail below, the present disclosure sets forth an improved assembly embodying advantageous alternatives to the conventional devices and approaches discussed above.

SUMMARY

According to an aspect of the present disclosure, a system includes a cylinder having a bore with a piston disposed therein, the piston moveable along the bore of the cylinder and having a passage therethrough. The system also includes a mixer disposed in the passage in the piston and including at least porous one mixing device, the at least one porous mixing device comprising a three-dimensional lattice defining a plurality of tortuous, interconnecting passages therethrough, and having physical characteristics to sufficiently mix the first and second components, which characteristics include a selected one or more of mean flow pore size, thickness and porosity.

According to another aspect of the present disclosure, a method of mixing materials using a system comprising a cylinder having a bore with a piston disposed therein, the piston moveable along the bore of the cylinder and having a passage therethrough, a mixer disposed in the passage in the piston and including at least one porous mixing device, the at least one porous mixing device comprising a three-dimensional lattice defining a plurality of tortuous, interconnecting passages therethrough, and having physical characteristics to sufficiently mix the first and second components, which characteristics include a selected one or more of mean flow pore size, thickness and porosity, and a source of a first component disposed either in the bore or the mixer. The method includes coupling a container to the passage, the container having a second component disposed therein, transferring the second component from the container to the bore through the passage, and transferring a mixture of the first and second components from the bore.

Additional aspects of the disclosure are defined by the claims of this patent.

BRIEF DESCRIPTION OF THE FIGURES

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

FIG. 1 is a perspective view of a mixing system according to the present disclosure;

FIG. 2 is a cross-sectional view of the mixing system of FIG. 1, as assembled;

FIG. 3 is an enlarged side view of the mixer used in the mixing system of FIG. 1;

FIG. 4 is a perspective view of the mixing system of FIG. 1, as assembled, with the first piston in a first state and the second piston in a second state to transfer material to the cylinder;

FIG. 5 is a perspective view of the mixing system of FIG. 1, with the first piston in a second state and the second piston in a first state to transfer material to the syringe;

FIG. 6 is a perspective view of the mixing system of FIG. 1, with the first piston in the second state and the second piston in the first state to transfer material to the syringe;

FIG. 7 is a perspective view of the mixing device of FIG. 1, with the first piston in the second state and the second piston in the second state and the cap removed to transfer material from the cylinder;

FIG. 8 is a perspective view of another mixing system according to the present disclosure;

FIG. 9 is a cross-sectional view of the mixing system of FIG. 8, as assembled;

FIG. 10 is a cross-sectional view of an alternative mixer for use in the mixing system of FIG. 8;

FIG. 11 is a cross-sectional view of a further alternative mixer for use in the mixing system of FIG. 8;

FIG. 14 is a fragmentary, perspective view of another mixing system, in a first state prior to assembly;

FIG. 15 is a partial cross-sectional view of the mixing system of FIG. 14, as assembled;

FIG. 16 is a fragmentary, perspective view of the mixing system of FIG. 14, with the piston in a first state to transfer material from the container to the vial; and FIG. 17 is a fragmentary, perspective view of the mixing system of FIG. 14, with the piston in a second state to transfer material from the vial to the container.

DETAILED DESCRIPTION

Figure 13:
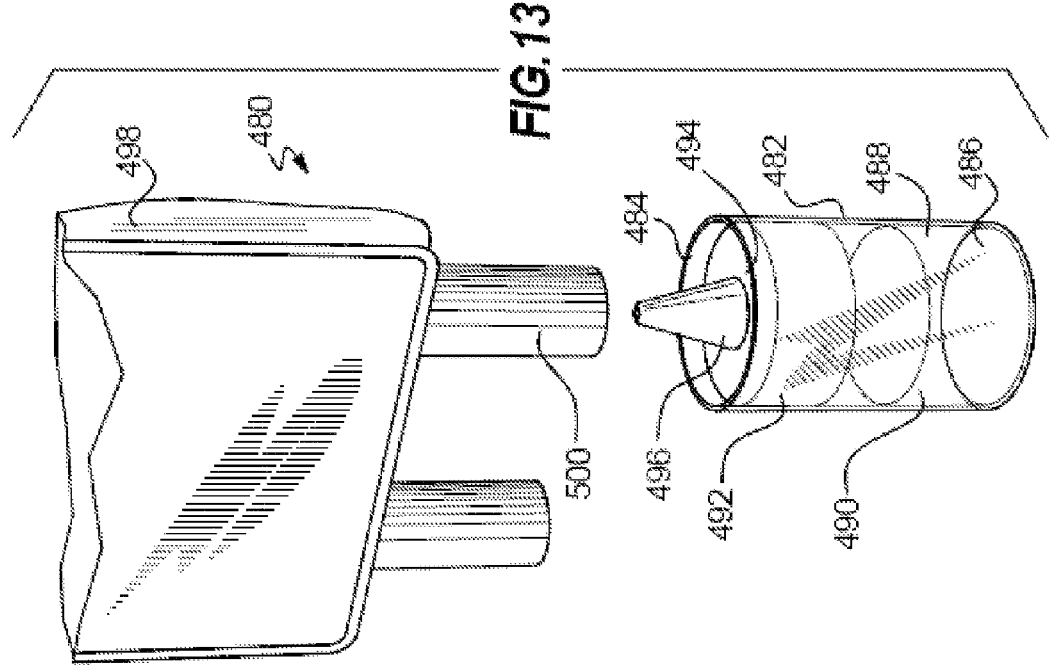
FIG. 13 is a fragmentary, perspective view of a still further mixing system according to the present disclosure.

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

FIGS. 1 and 2 illustrate a system 100 for mixing at least a first component with at least a second component, with the system 100 illustrated partially disassembled in FIG. 1 and as assembled in FIG. 2. The system 100 defines an arrangement similar to a telescoping syringe, as assembled. It will be recognized that the system 100 may be provided to the user in one or more pieces (in a sterile condition or prefilled condition) as a kit, the user assembling the pieces to define the system 100. The kit may include the components to be mixed, as well as adapters or dispensers for administering or applying the mixed components. The kit may be a disposable kit, such as a sterile disposable kit for medical applications. In the alternative to a kit, certain pieces of the system 100 may be provided to the user by the manufacturer, and then the user may separately obtain the other pieces that are then assembled to define the system 100. All such possibilities are within the scope of the present disclosure.

In particular, the system 100 includes a cylinder 102 having a wall 104 with an interior surface 106 defining a bore 108 (see FIG. 2). The bore 108 has a first end 110 and a second end 112, and may have a volume of from 0.5 to 50 ml according to certain embodiments. The first end 110 is open, while the second end 112 is closed, except for an opening 114 in communication with a male luer. The opening 114 may be selectively closed by covering the male luer with a cap 116.

Within the bore 108 is disposed a piston 130. The piston 130 may be formed from, for example, a siliconized rubber or a silicon-free rubber. In the latter case, the piston 130 may be a flurocoated rubber piston, such as may be obtained from Daikyo Seiko, Ltd. of Tokyo, Japan. Other materials that may be used for the piston 130 include, for example, polytetrafluoroethylene (PTFE) and other fluoropolymers.

The piston 130 is moveable along the bore 108 of the cylinder 102, and in particular is moveable between the first end 110 and the second end 112 of the bore 108. The piston 130 has a side surface 132 that abuts the interior surface 106 of the cylinder 102 that defines the bore 108. According to certain embodiments, the side surface 132 and the interior surface 108 form a seal therebetween, so as to prevent materials from moving across the seal. To this end, the piston 130 may be made of a flexible material that deflects inwardly when the piston 130 is disposed into the cylinder 102.

The piston 130 has a passage 134 that is defined therethrough. In particular, the piston 130 has opposing surfaces 136, 138, the surface 136 facing in the direction of the open end 110 of the bore 108 and the surface 138 facing in the direction of the closed end 112 of the bore 108. The passage 134 extends between the surfaces 136, 138, with a first opening 140 at the surface 136 and a second opening 142 at the surface 138. The surface 138 may be flat to assist in limiting void volume and potential loss of material in the bore 108.

As illustrated, a mixer 160 is disposed in the passage 134 in the piston 130 and includes at least one porous mixing device 162. The porous mixing device 162 may be a three-dimensional lattice defining a plurality of tortuous, interconnecting passages therethrough, and having physical characteristics to sufficiently mix the first and second components, which characteristics include a selected one or more of mean flow pore size, thickness and porosity. The porous mixing device may be made from a sintered material, such as a sintered glass, ceramic, metal or polymer. In a preferred embodiment, the porous mixing device is made from a sintered polyolefin, particularly a sintered polyethylene or a sintered polypropylene material and especially a sintered polypropylene material. According to the embodiment illustrated in FIGS. 1 and 2, the mixing device 162 may be formed from a VYON-F material, available from Porvair Technology, a Division of Porvair Filtration Group Ltd., of Wrexham, United Kingdom. Other alternative embodiments for the material used in the mixing device 162 may be found in U.S. Published Application No. 2009/0038701, which is incorporated herein by reference for all purposes.

According to the system 100 illustrated in FIGS. 1 and 2, the mixer 160 is attached to a syringe 190. Specifically, the mixer 160 may include a connector 192 that may be coupled to a first end 194 of the syringe 190 and through which a component disposed in the syringe 190 may pass for ejection from the syringe 190. As seen in greater detail in FIG. 3, the connector 192 may include a first housing section 196 and a second housing section 198. The first housing section 196 defines a male luer at a first end 200, and an enlarged receptacle 202 at a second end 204. The second housing section 198 has a first end 206 with a wall 208, which wall 208 mates with the receptacle 202 to define a chamber 210, and a second end 212 that is coupled to the remainder of the syringe 190. The at least one mixing device 162 is disposed in the chamber 210; according to certain embodiments, the at least one mixing device 162 is housed in the connector 192 so that material passing through the connector 192 must pass through the at least one mixing device 162. The connector 192 also includes a passage 214 that extends from the first end 200 of the first housing section 196 to the second end 212 of the second housing section 198.

In an alternate embodiment, the mixing device 162 may be formed so that it may be press fit within the interior of the male luer 200 such that fluid flowing through the passage 214 flows through the device 162. This eliminates the need of forming a chamber 210 to house the mixing device 162.

As best seen in FIG. 2, the connector 192, and particularly the male luer, depends through the passage 134 in the piston 130 so as to depend from the passage 134 out of the opening 142 and past the surface 138. In this fashion, the connector 192 is at least partially disposed in the passage 134 in the piston 130 so that the mixer 160 is disposed in the passage 134. As a consequence, the syringe 190 is coupled to the piston 130, and the passage 134 therethrough. This is an exemplary embodiment, and according to other embodiments, the connector 192 need not extend through the entire passage 134, but only some portion thereof, and still be coupled to the piston 130 and the passage 134.

Returning to the syringe 190, it will be recognized that the syringe 190 is of a typical structure. In this regard, the syringe 190 includes a cylinder 230 having a wall 232 with an interior surface 234 that defines a bore 236. The cylinder 230, and thus the bore 236, has the first end 194, mentioned above, and a second, open end 238. A piston 240 is received within the open end 238 of the bore 236, and is moveable within the bore 236 between the first end 194 and the second end 238. In particular, a connecting rod, push rod or pusher member 242 is coupled at a first end 244 to the piston 240 and has a thumb rest 246 defined at a second end 248. Finger rests 250 are also provided at the end 238 of the cylinder 230. The user may thus place his or her index and middle fingers on the finger rests 250 and his or her thumb on the thumb rest 246, and apply force to the pusher member 242 and piston 240 as the thumb is advanced in the direction of the fingers to advance the piston 240 along the cylinder 232.

According to the present embodiment, the mixing system 100 may be advantageously used with a two component system, wherein the two components are combined to produce a mixture. However, it will be recognized that the mixing system 100 may be used with a system that includes more than two components as well. In the two component system, a source of a first component may be disposed in either the bore 108 or the mixer 160, as will be explained in greater detail below. A source of a second component may be disposed in the syringe 190.

For example, the two component system may include a lyophilisate and its solvent (typically a liquid, such as water, in which the lyophilisate may be soluble or highly soluble). Alternatively, the two component system may include a powder and a liquid, or even two liquids. As to systems including a liquid component, while the component may be a liquid at the time of mixing, it is not required that the component be stored as a liquid. Instead, the liquid component may be stored in a frozen state, and then thawed at the time of mixing to resume its liquid state. The frozen component should be contrasted with a lyophilisate, which is produced by a process of freeze-drying, although both freezing and lyophilization may produce a form of the component that may maintain the potency and stability of the component better over time and that may extend the shelf-life for prolonged storage.

In regard to specific examples, the source of the first component may be a lyophilized protein cake disposed in the bore 108, while the source of the second component may be a diluent formulated to reconstitute, solubilize or resuspend the protein and may be disposed in the syringe 190. For that matter, rather than having a first component that is a solid and a second component that is a liquid, the nature of the components may be reversed, or the first and second components may both be liquids. For example, the source of the first component may be a liquid form of thrombin, and the source of the second component may be a liquid form of fibrinogen. As a still further variant, a gas may be used as well. Thus, a wide range of components may be used with the system 100.

A method of mixing materials using the system 100 may now be discussed relative to FIGS. 1 and 4-6. As seen in FIG. 1, the system 100 may be provided with the syringe 190 separated from the cylinder 102. As mentioned above, a cake of lyophilized protein may be disposed in the bore 108 of the cylinder 102, while a liquid is disposed in the syringe 190. To begin the process, the syringe 190 is coupled to the piston 130, and in particular the passage 134, with the cap 116 disposed to close off the opening 114 in the cylinder 102, for example by disposing, removably according to certain embodiments, the connector 192 in the passage 134 in the piston 130.

With the system 100 thus assembled, the second component is transferred from the syringe 190 to the bore 108 through the passage 134 by applying a force to the pusher member 242, and specifically to the thumb rest 246, in the direction indicated by the arrow in FIG. 4. This force is transmitted via the pusher member 242 to the piston 240 that is coupled to the pusher member 242. The protein solution may then be considered ready for administration.

Alternatively, the material in the bore 108 may be transferred from the bore 108 to the syringe 190, and transferred subsequently back and forth between the cylinder 102 and the syringe 190 to further mix the first and second components. The material may be transferred from the bore 108 to the syringe 190 in a number of different ways. For example, as illustrated in FIG. 5, force may be applied in the direction of the end 112 to the piston 130 via the syringe 190. As a consequence, the material will be directed into the bore 236 of the syringe 190, causing the syringe piston 240 to move in the opposite direction to the direction of the motion of the syringe 190. Alternatively, as illustrated in FIG. 6, a force may be applied to the syringe piston 240, thereby drawing the material from the bore 108 of the cylinder 102 into the bore 236 of the syringe 190. As a consequence of the motion of the material from the bore 108 to the bore 236, the piston 130 may move in the direction of the end 112 of the cylinder 102. The motion illustrated in FIG. 6 may be performed with the system 100 inverted so as to avoid aspiration of air into the syringe 190, and either motion may be assisted or performed automatically through the addition of a spring in the bore 108 that biases the piston 130 away from the end 112. In any event, material from the syringe 190 may be returned to the bore 108 through the passage 134 by applying a force to the pusher member 242 as shown in FIG. 4.

In addition, with the materials transferred to the cylinder 102, the syringe 190 may be detached, and a new syringe 190 attached to perform the back-and-forth transfer, or "swooshing," with an additional component. For example, a first syringe may be used to inject a liquid (e.g., calcium chloride solution) into the cylinder 102 to reconstitute a lyophilized form of thrombin. A certain amount of air will also be present in the cylinder 102 as well after this step. Once the first syringe is decoupled and removed, a new syringe containing fibrinogen may be coupled to the container 102 and used to mix the fibrinogen and the thrombin and air to create a "fibrin mousse": i.e., a fibrin mixture having a relatively higher volume of air (such as 125% by air volume) and a lower density than fibrin mixed without air. The fibrin mousse may, for example, allow application to the underside of a patient's body, such as for treatment of acute or chronic injuries such as a foot ulcer injury. The fibrin mousse obtained may also be spray dried to form fully or partially polymerized beads, lyophilized to form a sponge or grinded to obtain a haemostatic powder (dry fibrin glue), as described in U.S. Pat. No. 7,135,027, as incorporated herein by reference.

In another example, the components may include an oil phase in one of the cylinder 102 or the syringe 190 and an aqueous phase in the other, without the addition of air. The swooshing between the cylinder 102 and the syringe 190 produces an emulsion or a pre-emulsion of desired globule size. In a more particular example, the oil phase may include soya oil (200 ml) and egg phosphatide (12 g), and the aqueous phase may include water (200 ml), glycerol (25 g) and sodium oleate (0.3 g). While not required, the oil phase may be frozen, and then thawed before mixing without affecting the emulsion or pre-emulsion formed.

It should be noted that testing has suggested that the number of transfers between the containers does not have a significant impact on the diameter of the bubbles formed when mixing fibrinogen or thrombin with air to produce a foam. On the other hand, it is believed that the type of material utilized for the mixer and the air fraction influence the diameter of the bubble formed. That is, once the material has been transferred four times between the containers using a mixing device made of the VYON-F material, a homogenous foam with an average bubble diameter of approximately 50 μm is formed, and additional transfers do not change the diameter or the size dispersion (normalized fluctuation of the average bubble diameter) appreciably. On the other hand, increasing the air fraction from 50% to 70% may increase the average bubble diameter from approximately 50 μm to approximately 65 μm, as may changing the material used as the mixer. It is further believed that the results of testing using fibrinogen are applicable to fibrin as well.

It is believed that the method of mixing using the system 100 discussed above may be optimized (through optimization of the mixer) to provide a mixture that avoids the clogging of delivery devices during administration, and the potential risk of injecting an incompletely dissolved drug. Also, a container containing a lyophilisate and its solvent typically would be shaken or swirled to favor solubility, and the mixer used in the system 100 is intended to remove the need for such shaking or swirling. However, it should be understood that the method of mixing using the system 100 discussed above may be combined shaking or swirling, if desired.

The mixture of the two components may be transferred from the system 100 to a patient in a number of different ways. In keeping with the discussion above, a force may be applied in the direction of the end 112 to the piston 130 via the syringe 190 to direct the material into the bore 236 of the syringe 190, or force may be applied in the direction of the end 110 to the syringe piston 240 to draw the material into the bore 236 of the syringe 190. The syringe 190 and the connector 192 may then be removed from the piston 130, and used in the traditional manner (e.g., the syringe 190 may be manipulated separately of the cylinder 102 to inject the mixture into a set via a needleless connector, into a port of a pouch or bag, through a stopper of a vial, or in combination with a needle or pointed cannula for subcutaneous or intramuscular injection) with or without the connector 192 coupled to the syringe 190. Alternatively, user may remove the cap 116 from the male luer, and force may be applied in the direction of the end 112 to the piston 130 via the syringe 190 and the pusher member 242 to transfer the mixture of the first and second components from the bore 108 through the opening 114, as illustrated in FIG. 7.

According to other variants, the system 100 or the syringe 190 may be coupled to additional adapters or dispensers. For example, the syringe 190 may be coupled to a cannula or to an accessory, such as the DUPLOJECT dispenser, marketed by Baxter AG and mentioned above. Other alternatives may include tubes or tubing segments, needles, luer tips, catheter, spray tips or spray devices, depending on the desired form in which the combined mixture is to be administered or applied and/or the work surface. These additional devices may be coupled as a permanent attachment, through the use of an adhesive for example, or a releasable attachment, through the use of a friction fit, press fit or luer lock, for example.

As noted above, while the system 100 was discussed above with a cake of lyophilized protein disposed in the bore 108 of the cylinder 102 and a liquid disposed in the syringe 190, circumstances may be reversed. That is, the cake may be disposed in the bore 236 of the syringe 190, and the liquid may be contained in the cylinder 102. According to such an embodiment, the liquid may first be transferred from the cylinder 102 to the syringe 190, using a method similar to that illustrated in FIGS. 5 and 6 to transfer the liquid to the syringe 190.

In fact, according to a related variant, the syringe 190 may be coupled to the piston 130 of an initially empty cylinder 102. The cap 116 is removed from the male luer, and force may be applied to the piston 130 via the syringe 190 to draw liquid into the bore 108 of the cylinder 102. The cap 116 may then be replaced, and the method may progress as stated above, with the liquid being transferred from the now filled or partially-filed cylinder 102 to the syringe 190 to reconstitute the cake disposed in the bore 236.

The present disclosure also is not limited to the specific structure illustrated in FIGS. 1-7. Further variants are illustrated in FIGS. 8-17, illustrating the wide range of structures that may be used, and how those structures may be used to incorporate different sources of components into the mixing system.

FIGS. 8 and 9 illustrate a variant system 300 similar to that illustrated in FIGS. 1-7. That is, the system 300 has the general form of a telescoping syringe, with a cylinder 302 with a bore 304 in which is disposed a piston 306, moveable between a first end 308 and a second end 310. The piston 306 includes a passage 312 (best seen in FIG. 9) that passes through the piston 306 from a first surface 314 to a second surface 316. The system 300 also includes a syringe 320 that may be coupled to the piston 306, and in particular to a passage 312 in the piston 306.

The system 300 also includes a mixer 330 that is disposed in the passage 312 through the piston 306. The mixer 330 includes at least one mixing device 332 that may be a three-dimensional lattice defining a plurality of tortuous, interconnecting passages therethrough, and having physical characteristics to sufficiently mix first and second components, which characteristics include a selected one or more of mean flow pore size, thickness and porosity, like the mixing device 162. However, rather than the mixer 330 being defined by a connector coupled to the syringe and removable from the piston, as was the case with the system 100, the mixer 330 is defined by a connector 340 attached to the piston 306.

As seen in FIG. 9, the connector 340 may include a housing 342, which may simply be a cylindrical wall. The housing 342 has an outer surface 344 that abuts an inner surface 346 of the piston 306 defining the passage 312. The housing 342 may simply be press-fit into place within the piston 306, although other methods of joining may be used to attach the outer surface 344 of the housing 342 to the inner surface 346 of the piston.

The mixing device 332 is secured within the housing 342, and in particular a passage 348 through the housing 342 between a first end 350 and a second end 352. The passage 348 may have a stepped inner surface, so as to accurately seat the mixing device 332 within the passage 348. Alternatively, a spacer or other mechanical fitting may be disposed within the passage 348 to define a shoulder, similar to the stepped inner surface, for accurate seating of the mixing device 332 within the passage 348. As illustrated, the mixing device 332 is simply disposed within the passage 348 without the use of a stepped inner surface or spacer. Providing a snap fit between the inner surface of the passage 348 and mixing device 332 may also contribute to retaining the mixing device 332 within the housing 342. The mixing device 332 may be secured to the housing 342 using ultrasonic welding or other attachment techniques.

The first end 350 of the housing 342 may define a female luer, for receiving a male luer of the syringe 320, or otherwise be adapted to form a connection with a second connector provided on a container. The mating of the male and female luers couples the syringe 320 to the mixer 330. It will be appreciated that other types of connections are possible, and that the male and female luers may instead be defined on the mixer 330 and the syringe 320, respectively.

It will be recognized that while the systems 100, 300 were illustrated having mixers 160, 330 with a single mixing device 162, 332, the mixers could include instead two, three or more mixing devices. In such an embodiment, the individual mixing devices might have different characteristics, such as porosity, mean pore size or length, to provide a beneficial effect. Varying the characteristics of the mixing devices may well increase the thoroughness of mixing as the components pass through the mixer.

Furthermore, as illustrated in FIGS. 10 and 11, if additional mixing devices are used, the mixing devices may be spaced apart. For example, FIG. 10 illustrates a mixer 380 having two mixing devices 382, 384 that are spaced apart along a passage 386 defined by a housing 388 to define a volume 390 therebetween. Similarly, FIG. 11 illustrates a mixer 400 having two mixing devices 402, 404 that are spaced apart along a passage 406 defined by a housing 408 to define a volume 410 therebetween, the volume 410 being larger than the volume 390. The spacing between the mixing devices may vary, as illustrated in FIGS. 10 and 11, according to the requirements of a particular system.

The variants illustrated in FIGS. 10 and 11 provide for several additional options for the mixer. The volume 390, 410 may provide for "Stop and Go" flow through the mixer 380, 400, which may enhance the mixing of materials passing through the mixer 380, 400, particularly in a system where the materials are transferred back and forth between the cylinder and the syringe. In addition, the source of one of the components of the system being mixed may be disposed in the volume 390, 410, instead of in the cylinder or the syringe, for example. This may be particularly useful when used with a system such as that of fibrinogen and thrombin, where the catalyst (thrombin) only needs to be present at low concentrations; placing the thrombin in the volume 390, 410 eliminates the need to use equal volumes of the two components.

In regard to "Stop and Go" flow, it should be understood that this refers to the fact that the flow is intermittently started and stopped. It is believed that "Stop and Go" flow enhances the mixing process. For example, it has been found that the presence of fibrin between the two mixing devices increases when the distance between them increases. A distance of about 3 mm and above may result in good fibrin formation of sufficient homogeneity where the two mixing devices have a diameter of 3-5 mm and a thickness of 1.5-3 mm. Of course, in such a setting, one limitation on increasing the efficiency of the mixing of the components is the likelihood that significant fibrin will be formed on the mixing devices or between the mixing devices. By way of example and not limitation, for a two mixer device, a distance of about 4 mm may achieve sufficiently thorough mixing as well as avoid significant generation of fibrin on or between the two mixing devices. As a general matter, it will be recognized that the distances between the mixing devices may vary based on different designs and/or the different parameters that are employed in such design, as well as the components mixed and the mixed product, such that the distance between mixing devices should not be limited to only the above discussed values or ranges.

In regard to use of the volume 390, 410 for a source of a component to be mixed, according to certain embodiments of the present disclosure, where the distance between the mixing devices is 3 mm, the volume may be approximately 18 µl. As a consequence, if a second component having a concentration of 100 IU/ml is disposed in the volume, then 1.8 IU of the second component may be immobilized between the mixing devices. Similarly, for concentrations of 1000 IU/ml and 10,000 IU/ml, 18 IU and 180 IU will be immobilized in the volume, respectively. This permits the amount of the component present to be controlled according to the requirements of the user and the purpose of the application; for example, where the second component is a catalyst, the amount of the second component immobilized in the volume may control the kinetic of polymerization.

Experiments have been performed using mixers similar to those illustrated in FIGS. 10 and 11, wherein freeze-dried thrombin has been introduced into a volume defined between two mixing devices made of the VYON-F material. In particular, mixers were prepared using 200 µL of a solution of thrombin having a concentration of 500 IU/mL freeze-dried between the mixing devices. These mixers were used with a syringe-type source containing either 0.5 or 1.0 ml of fibrinogen. In all experiments, the fibrin product provided acceptable results: The material flowed freely from the dispenser system in the first set of experiments, and polymerization occurred either in about 30 minutes to 1 hour.

In fact, according to other variants, at least one of the components may be immobilized within a mixing device itself, instead of in a volume between two mixing devices. According to an exemplary embodiment for a system of fibrinogen and thrombin being used to generate fibrin, the thrombin may be immobilized by freeze-drying the thrombin within the porous structure of the mixing device. To prepare the mixing device, a solution of this component may be passed through the mixing device. The mixing device is freeze-dried with the component in place within the porous structure of the mixing device.

In fact, where the pore volume (or porosity) is known, a rough approximation may be made for the amount of thrombin (or other component) present in the mixing device. Assuming a mixing device having a diameter of 3.8 mm, a thickness of 1.5 mm, and a porosity of 45%, the void volume that may be filled with the second component is 7.65 µl. Again, the amount of second component immobilized will be dependent upon the concentration of the solution used, but for a solution with a concentration of 100 IU/ml, 0.7 U of the second component may be immobilized in the mixing device.

Along similar lines, the component may be immobilized by adsorption of the component on the surface of the porous structure of the mixing device. Using the example of a system of thrombin and fibrinogen, adsorption may provide additional advantages in that the volume of the diluent of thrombin used may permit a doubling of the volume of the diluent of fibrinogen used, leading to a reduction in the viscosity of the fibrinogen. Given that the dilution/viscosity curve is non-linear, the doubling of the volume of diluent may lead to a viscosity of between 5 and 20 cps (centipoise).

In particular, it has been shown experimentally that thrombin may be adsorbed on the surface of a porous structure made of the VYON-F material described above. In particular, thrombin at a concentration of 500 IU/ml was diluted with a carbonate/bicarbonate buffer (pH 9.0) to obtain thrombin at a concentration of 250 UI/ml. The mixing device made of the VYON-F material was placed in 50 µl of the thrombin for 10 minutes, and then the mixing device was washed with distilled water. It is believed that the washing with distilled water will cause any thrombin not adsorbed to the surface of the mixing device to be removed.

As confirmation of the fact that thrombin was adsorbed to the surface of the mixing device as a consequence of this process, 100 µl of a synthetic substrate, SQ150, at a concentration of 1.4 µmole/ml (0.85 m/ml) was added. The substrate couples to paranitroaniline, permitting optical density readings at wavelengths of approximately 400 nm. Based on these readings, it has been estimated that 2.2 IU was adsorbed to the mixing device. It is believed that additional thrombin could be adsorbed with an increase in the specific surface of the mixing device. It is also believed that different materials may permit an increase in the adsorption of the thrombin, and that the thrombin may be adsorbed to the material of the mixer in which the mixing device is disposed, if the adsorption process is carried out with the mixing device already in place as illustrated in FIGS. 10 and 11.

FIGS. 12-17 illustrate still further variants to the systems 100, 300. In the systems illustrated FIGS. 12-17, the system is no longer in the form of a telescoping syringe. Rather, FIGS. 12-17 illustrate that it is not necessary that a cylinder be used that has an open end and a selectively closed opposing end. FIGS. 13-17 also illustrate that it is not necessary to use a syringe, but that other containers may be used in substitution for the syringe.

Figure 12:
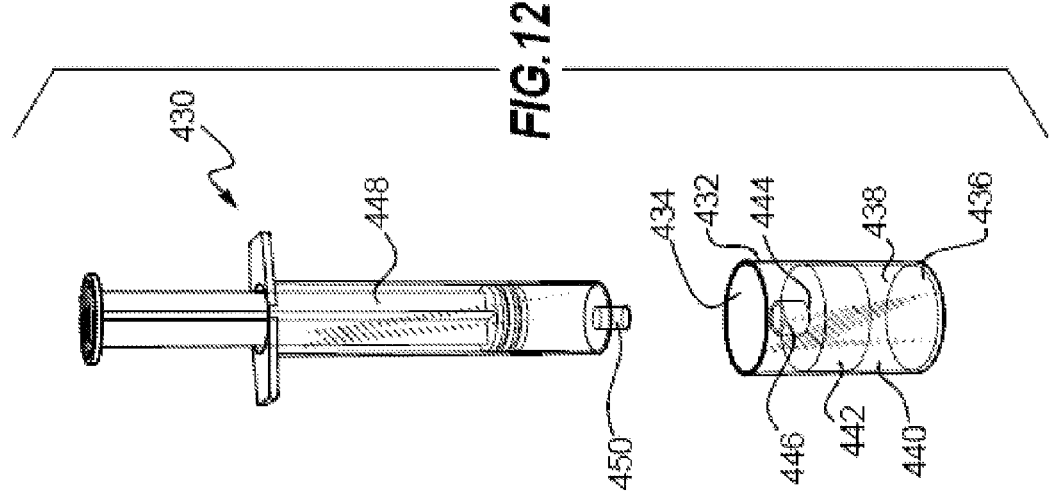
FIG. 12 is a perspective view of a further mixing system according to the present disclosure.

Turning first to FIG. 12, a system 430 is illustrated. As noted above, the system 430 includes a cylinder 432 having a first, open end 434 and a second, closed end 436. The cylinder 432 has a wall 438 that defines a bore 440 in which a piston 442 is disposed, which piston 442 is moveable between the first and second ends 434, 436. The piston 442 has a passage 444 in which is disposed a mixer 446 having at least one mixing device. The system 430 also includes a syringe 448 with a male luer 450 that is coupleable to the mixer 446.

It will be recognized that the system 430 shares much in common with the system 300, except for the fact that the cylinder 432 cannot be opened at its second end 436. As such, material within the bore 440 of the cylinder 432 cannot be aspirated from the second end 436, as may be done in the systems 100, 300 by removal of the caps, for example cap 116. However, this does not prevent the syringe 448 from being used to draw the material from the cylinder 432 using a method similar to that illustrated in FIG. 5 or 6.

FIG. 13 illustrates a further system 480 that does not include a cylinder with a selectively closed end or a syringe. Instead, the system 480 includes, similar to system 430, a cylinder 482 having a first, open end 484 and a second, closed end 486. The cylinder 482 has a wall 488 that defines a bore 490 in which a piston 492 is disposed, which piston 492 is moveable between the first and second ends 484, 486. The piston 492 has a passage 494 in which is disposed a mixer 496 having at least one mixing device, as described in greater detail below. The system 480 also includes a container 498, which may be in the form of a pouch or flexible bag as illustrated, with a port assembly 500 that is coupleable to the mixer 496. According to such a variant, the port assembly 500 is pressed against the piston 492 of the piston 492 is advanced in the direction of the port assembly 500 so as to move the piston 492 between the ends 484, 486, and thereby pass the material in the cylinder 482 into the container 498 through the mixer 496.

In fact, the cylinder 482 and the container 498 may be manufactured as a single unit. According to such an embodiment, the cylinder 482 and the container 498 may be manufactured so that the cylinder 482 must be manipulated (e.g., rotated) to open the communication between the cylinder 482 and the container 498. In fact, the wall of the container 498 may be compressed to force liquid into the cylinder 482 so as to reconstitute a lyophilized material contained in the cylinder 482. The piston 492 may then be advanced along the bore 490 toward the closed end 486, to move the reconstituted material through the mixer 496 into the container 498.

FIGS. 14-17 illustrate a further system 550 very similar to system 480. For example, system 550 includes a cylinder 552 having a first, open end 554 and a second, closed end 556. The cylinder 552 has a wall 558 that defines a bore 560 in which a piston 562 is disposed, which piston 562 is moveable between the first and second ends 554, 556. Unlike the embodiment in FIG. 13, the piston 562 has a male luer 564, or is otherwise adapted to form a connection with a second connector provided on a container, in which is disposed a mixer 566 (see FIG. 15) having at least one mixing device.

The system 550 also includes a container 568, which may be in the form of a pouch or flexible bag as illustrated, with a rigid port assembly 570 (made of a material such as high density polyethylene (HDPE), for example). Unlike the embodiment of FIG. 13, the port assembly 570 has a female luer 572 with a valve 573 (see FIG. 15), similar to a Halkey-Roberts luer device. In fact, the piston 562 may have a threaded collar 574 formed about the male luer 564, and the female luer 572 may have a threaded surface 576, the threads of the threaded collar 574 mating with the threaded surface 576 to securely attach the male and female luer connections 564, 572. While the connectors 564, 572 are illustrated as aligned with a longitudinal axis 578 of the port 570, this is not required in all embodiments; a "T" connection may be used instead where the connectors 564, 572 are aligned orthogonally to the longitudinal axis 578 of the port 570.

According to one embodiment of the present disclosure, the container 568 contains a diluent or solvent, and the cylinder 552 contains a lyophilisate. According to this embodiment, the system 550 may be used according to the following exemplary method.

As seen in FIG. 14, the container 568 and the cylinder/piston 552, 562 may be initially separated. As seen in FIG. 15, the male and female luer connections 564, 572 may be brought together, and rotated relative to each other to engage the threaded surface 576 with the threaded collar 574 to securely attach the connections 564, 572. If there is a vacuum initially within the cylinder 552, then liquid will be drawn down from the container 568 into the cylinder 552 through the action of the vacuum (see arrow "A" in FIG. 16). Otherwise, the liquid from the container 568 may be aspirated manually by moving or pulling the cylinder 552 away from the container 568.

Once the liquid has been transferred to the cylinder 552 and the lyophilisate is reconstituted (or even before reconstitution, depending on solubility and instruction of use), the cylinder 552 may be moved or pushed in the direction of the container 566 (see FIG. 17). Because of the rigidity of the port assembly 570, the piston 562 will move relative to the cylinder 552, forcing the material in the bore 560 to be ejected through the connectors 564, 572 and the port assembly 570 into the container 568 (see arrow "B" in FIG. 17). As will be recognized, the relative length of the port assembly 570 relative to the depth of the cylinder 552 between open and closed ends 554, 556 may be selected to permit the entire contents of the cylinder 552 to be ejected from the bore 560 into the container 568.

It will be recognized that the preceding steps (compare FIGS. 16 and 17) may be repeated, with the cylinder 552 being alternatively pulled away from and pushed toward the container 568. In doing so, the contents of the cylinder 552 and material from the container 568 will pass repeated through the mixer 566, similar to the "swooshing" motion described above. The repetition of these steps may ensure optimized mixing of the lyophilisate and the diluent or solvent, and transfer of the reconstituted material to the container 568. The repetition of these steps may also help avoid concentration of the reconstituted material inside of the port assembly 570, which could lead to administration of a bolus from the container 568 during use.

Once the mixing has been completed, the connectors 564, 572 may be detached from each other, by rotating the cylinder 552 relative to the port assembly 570. The cylinder 552/piston 562 may then be discarded. The valve associated with the connector 564 will assist in ensuring that the solution in the container 568 remains sterile, and that the container 568 remains fluid-tight until administered to a patient, intravenously for example.

Having thus discussed the structure and operation of various embodiments of the system, additional comments may be made regarding the components that may be mixed using such a system. As specifically mentioned above, the mixing devices may be used with a two-component system to produce fibrin. Alternatively, the mixing devices may be used with a two-component system to reconstitute a protein cake. As a still further alternative, the mixing devices may be used to reconstitute any of a number of different materials that may be lyophilized, to mix powdered forms of the material (e.g., CEPROTIN Protein C Concentrate, which trademarked product is available from Baxter Healthcare Inc.) with a liquid, or even to mix two liquid components (e.g., FLEXBUMIN or BUMINATE Albumin (Human), which trademarked products are available from Baxter Healthcare Inc.).

Thus, according to certain embodiments, the mixing devices according to the present disclosure may be used to reconstitute a protein cake. In particular embodiments, the protein cake may contain a material used for the treatment of hemophilia, such as an antihemophilic factor (recombinant) such as ADVATE or RECOMINATE, an antihemophilic factor (human) such as HEMOPHIL M, or an anti-inhibitor coagulant complex such as FEIBA VH, which trademarked products are available from Baxter Healthcare Inc. According to other embodiments, the protein cake may contain immunoglobulins such as GAMMAGARD, which trademarked product is available from Baxter Healthcare Inc. In still other embodiments, the protein cake may include a material used for the treatment of pulmonary disease, such as an alpha-1-proteinase inhibitor (human) such as ARALAST, which trademarked product is available from Baxter Healthcare Inc.

The solvent used to reconstitute the protein cake may be organic, inorganic, or a mixture of both. Many times, the solvent is a hydrophilic solution containing electrolytes. Commonly, water may be used in combination with solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

According to other embodiments, the mixing devices according to the present disclosure may be used to mix liquid forms or to reconstitute lyophilized forms of antibiotics such as amoxicillin/clavulanic acid (AUGMENTIN, AMOXICILLIN WOK, CO-AMOXICLAV WOK), tazobactam/piperacillin (TAZOCIN), ampicillin/sulbactam (UNASYN), cilastatin/imipenem (TIENAM), ceftriaxone (FIDATO, ROCEPHIN, KOCEFAN), cefazolin (CEFAMEZIN, CEFAZOLIN SANDOZ), meropenem (MERREM, MERONEM), ceftazidime (GLAZIDIM), ampicillin (AMPLITAL, PENTREXYL), teicoplanine (TARGOSID), penicillin G (CRYSTAPEN, PENICILLIN—PHA), cefuroxime (CEFUROXIME FY4, ZINACEF), flucloxacillin (FLUCLOXACILLIN WOK), clarithromycin (KLARICID), vancomycin (VANCOCIN), floxacillin (FLOXAPEN), and amikacin (AMIKIN).

More generally, the mixing of a wide variety of materials in liquid or powdered form or the reconstitution of a wide variety of lyophilized materials may be achieved with the system according to the present disclosure. The drugs may be for the treatment of various diseases and conditions, including the drugs and conditions described in U.S. Pat. Nos. 6,186,982 and 7,560,100, which patents are incorporated herein by reference for all purposes.

It should also be noted that it is also possible to introduce other additive agents, such as antibiotics, drugs or hormones to one or more of the sources. For example, the source of the first component may include other components as well as fibrinogen. Similarly, the source of the second component may include a further component besides thrombin. According to one such example, the thrombin may contain calcium phosphate granules. Other alternatives may be found in U.S. Published Application No. 2009/0038701, which has been incorporated herein by reference for all purposes, above, as well as coagulation factors activated or not, as VII, X prothrombin, VIIIc antibodies, and Trypsin type III.

With this by way of background, it should also be understood that a method of mixing materials is also provided herein as an aspect of the present disclosure. This method may involve use of a system including a cylinder having a bore with a piston disposed therein, the piston moveable along the bore of the cylinder and having a passage therethrough, a mixer disposed in the passage in the piston and including at least one porous mixing device, the at least porous one mixing device comprising a three-dimensional lattice defining a plurality of tortuous, interconnecting passages therethrough, and having physical characteristics to sufficiently mix first and second components, which characteristics include a selected one or more of mean flow pore size, thickness and porosity, and a source of a first component disposed either in the bore or the mixer. The method may include coupling a container to the passage, the container having a second component disposed therein, transferring the second component from the container to the bore through the passage, and transferring a mixture of the first and second components from the bore.

The method may also include transferring the mixture of the first and second components from the bore into the container, and transferring subsequently the mixture of the first and second components from the container to the bore.

According to certain aspects, in combination with the method according to either foregoing paragraph, the cylinder may have an opening with a cap disposed over the opening, and the method may include removing the cap from over the opening, and transferring the mixture of the first and second components from the bore through the opening. In addition, the container may be a syringe having a syringe bore with a syringe piston disposed therein, and the method may include applying force in a first direction to the syringe piston to transfer the second component from the container to the bore through the passage, and applying force in the first direction to the piston via the syringe to transfer a mixture of the first and second components from the bore through the opening in the cylinder.

According to other aspects, in combination with aspects of the method described earlier herein, the container may be a syringe having a syringe bore with a syringe piston disposed therein, and the method may include applying force in a first direction to the syringe piston to transfer the second component from the container to the bore through the passage, and applying force in the first direction to the piston via the syringe to transfer a mixture of the first and second components from the bore into the syringe bore.

According to still other aspects, in combination with aspects of the method described earlier herein, the method may include transferring the mixture of the first and second components from the bore to a second container. In addition, the method may include applying force to the piston via the second container to transfer the mixture of first and second components from the bore to the second container.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A system comprising:
a cylinder having a bore with a piston disposed therein, the piston moveable along the bore of the cylinder and having a passage therethrough;
a mixer disposed in the passage in the piston and including at least one porous mixing device, the at least one porous mixing device comprising a three-dimensional lattice defining a plurality of tortuous, interconnecting passages therethrough, and having physical characteristics to sufficiently mix first and second components, which characteristics include a selected one or more of mean flow pore size, thickness and porosity; and
a container attachable to the passage and moveable with the piston,
wherein at least one of the bore and the mixer has a first component disposed therein and the container has a second component disposed therein, the second component transferred from the container to the bore through the passage in a first state, and a mixture of the first and second components transferred from the bore in a second state, and
wherein the mixture of the first and second components is transferred from the bore to the container in a third state, and the mixture of first and second components is subsequently transferred from the container to the bore in a fourth state.

2. The system according to claim 1, wherein the container comprises a syringe.

3. The system according to claim 1, wherein the container comprises a flexible bag.

4. The system according to claim 1, wherein the cylinder has a first, open end and a second, closed end, the piston being moveable between the first end and the second end.

5. The system according to claim 1, wherein the cylinder has a first, open end and a second end with an opening with a cap disposed over the opening, the piston being moveable between the first end and the second end.

6. The system according to claim 1, wherein the mixer comprises first and second mixing devices, the first and second mixing devices being spaced apart to define a volume therebetween.

7. The system according to claim 1, wherein the mixer comprises a source of the first component immobilized therein.

8. The system according to claim 1, wherein the at least one porous mixing device comprises a sintered material.

9. The system according to claim 8, wherein the at least one porous mixing device comprises a porous material selected from the group consisting of polymer, glass, ceramic and metal.

10. The system according to claim 9, wherein the at least one porous mixing device comprises a material selected from the group consisting of polypropylene and polyethylene.

11. The system according to claim 1, wherein the cylinder has an opening, and the mixture of the first and second components is transferred from the bore through the opening in the second state.

12. The system according to claim 1, wherein the mixture of the first and second components is transferred from the bore to a second container in the second state.

13. The system according to claim 12, wherein the piston and the second container move in a first direction to transfer the mixture of first and second components from the bore to the second container in the second state.

14. A system comprising:
a cylinder having a bore with a piston disposed therein, the piston moveable along the bore of the cylinder and having a passage therethrough;
a mixer disposed in the passage in the piston and including at least one porous mixing device, the at least one porous mixing device comprising a three-dimensional lattice defining a plurality of tortuous, interconnecting passages therethrough, and having physical characteristics to sufficiently mix first and second components, which characteristics include a selected one or more of mean flow pore size, thickness and porosity; and
a container coupled to the passage,
wherein at least one of the bore and the mixer has a first component disposed therein and the container has a second component disposed therein, the second component transferred from the container to the bore through the passage in a first state, and a mixture of the first and second components transferred from the bore in a second state,
wherein the cylinder has an opening, and the mixture of the first and second components is transferred from the bore through the opening in the second state, and
wherein the container comprises a syringe having a syringe bore with a syringe piston disposed therein, the syringe piston moves in a first direction to transfer the second component from the container to the bore through the passage in the first state, and the piston and the syringe piston move in the first direction to transfer a mixture of the first and second components from the bore through the opening in the cylinder in the second state.

15. A system comprising:
a cylinder having a bore with a piston disposed therein, the piston moveable along the bore of the cylinder and having a passage therethrough;
a mixer disposed in the passage in the piston and including at least one porous mixing device, the at least one porous mixing device comprising a three-dimensional lattice defining a plurality of tortuous, interconnecting passages therethrough, and having physical characteristics to sufficiently mix first and second components, which characteristics include a selected one or more of mean flow pore size, thickness and porosity; and
a container coupled to the passage,
wherein at least one of the bore and the mixer has a first component disposed therein and the container has a second component disposed therein, the second component transferred from the container to the bore through the passage in a first state, and a mixture of the first and second components transferred from the bore in a second state, and
wherein the container comprises a syringe having a syringe bore with a syringe piston disposed therein, the syringe piston moves in a first direction to transfer the second component from the container to the bore through the passage in the first state, and the piston and the syringe move in the first direction to transfer a mixture of the first and second components from the bore into the syringe bore in the second state.

* * * * *